United States Patent
Moser

(10) Patent No.: US 7,801,626 B2
(45) Date of Patent: Sep. 21, 2010

(54) INSTRUMENTED RETRIEVABLE IMPLANTABLE DEVICE

(76) Inventor: Raymond Moser, Chemin du Croset 11, CH-1024 Ecublens (CH)

( * ) Notice: Subject to any disclaimer, the term of this patent is extended or adjusted under 35 U.S.C. 154(b) by 129 days.

(21) Appl. No.: 11/304,797

(22) Filed: Dec. 16, 2005

(65) Prior Publication Data

US 2006/0100531 A1    May 11, 2006

Related U.S. Application Data

(63) Continuation of application No. PCT/EP2004/051121, filed on Jun. 15, 2004.

(30) Foreign Application Priority Data

Jun. 17, 2003   (EP)   ................................. 03101769

(51) Int. Cl.
*A61N 1/05* (2006.01)
(52) U.S. Cl. ..................... 607/126; 607/36; 600/302
(58) Field of Classification Search ............... 607/36, 607/119, 126–128; 600/302
See application file for complete search history.

(56) References Cited

U.S. PATENT DOCUMENTS

| | | |
|---|---|---|
| 4,721,118 A | 1/1988 | Harris |
| 4,886,065 A | 12/1989 | Collins, Jr. |
| 5,282,845 A | 2/1994 | Bush et al. |
| 5,855,592 A | 1/1999 | McGee et al. |
| 5,954,761 A | 9/1999 | Machek et al. |
| 6,136,021 A * | 10/2000 | Tockman et al. ............ 607/119 |
| 6,409,674 B1 * | 6/2002 | Brockway et al. ........... 600/486 |
| 6,416,493 B1 * | 7/2002 | Del Giglio ............... 604/96.01 |
| 6,442,413 B1 | 8/2002 | Silver |
| 2003/0225443 A1 * | 12/2003 | Kiran et al. ................. 607/119 |

FOREIGN PATENT DOCUMENTS

EP    0553580    12/1992

* cited by examiner

*Primary Examiner*—Scott M Getzow
*Assistant Examiner*—Joseph M Dietrich
(74) *Attorney, Agent, or Firm*—Blank Rome LLP

(57) ABSTRACT

Instrumented retrievable implantable device (2), comprising an expandable section, for placement inside a body lumen, preferably in a blood vessel. The device (2) comprises a joined sensor (70) for monitoring one or more physiological parameter for diagnostic or therapeutic purposes. Data access is assured by a passive RF transponder, in communication with an external readout unit or an implanted device, providing as well to the energy supply of the sensor (70). The shape of the device of the invention (2) allows repositioning and retrieval by micro-invasive methods, by means of a link section (20) capable of being coupled with a grabbing device (45) mounted on a catheter (40).

23 Claims, 5 Drawing Sheets

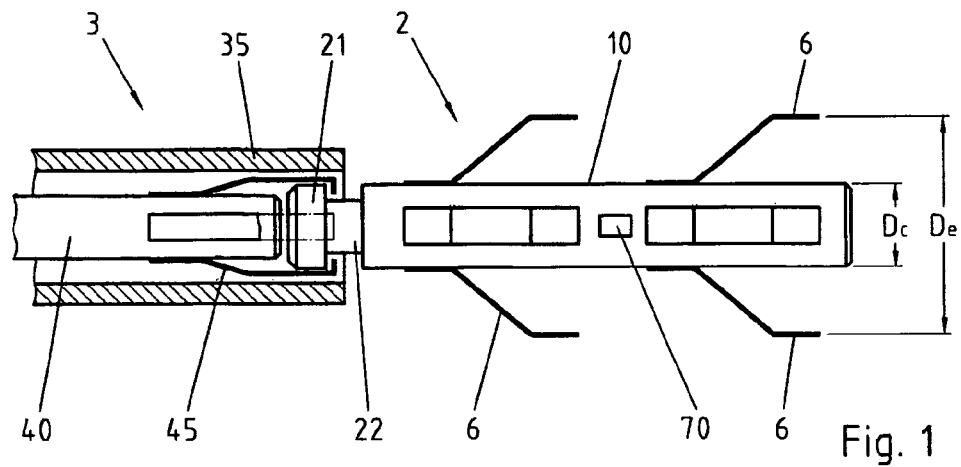
Fig. 1
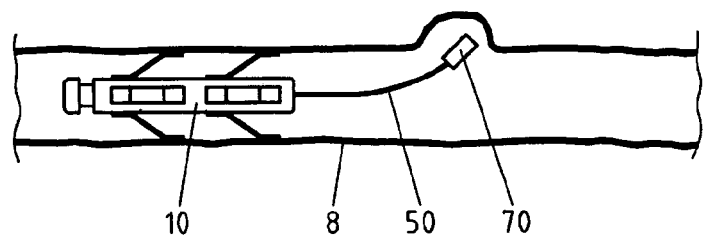
Fig. 3
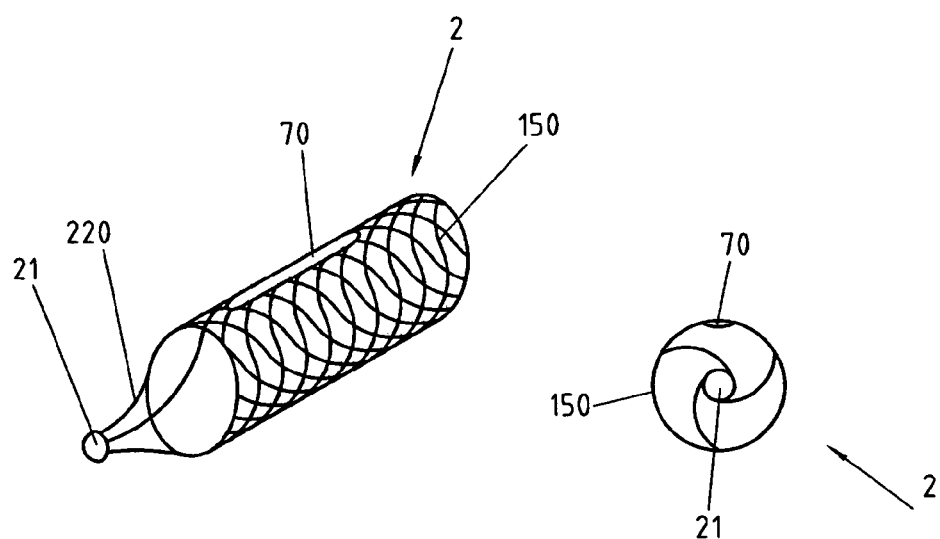
Fig. 4a
Fig. 4b

US 7,801,626 B2

INSTRUMENTED RETRIEVABLE IMPLANTABLE DEVICE

REFERENCE DATA

This application is a Continuation of Int'l Patent Appln. No. PCT/EP2004/051121, Publication No. WO/2004/110263, filed on Jun. 15, 2004, which is hereby incorporated by reference.

FIELD OF THE INVENTION

The present invention deals with an implantable device, comprising a removable part, for retrievably securing the device inside a body lumen, and a sensor, for measuring, logging and/or transmitting relevant body parameters.

Implantable devices have long been applied, in particular in conjunction with balloon angioplasty, to restore proper flow in constricted blood vessels. In this application the blood vessel is expanded with an inflatable balloon, guided into the desired section of the vessel by means of a catheter. The intraluminal or intravascular device or stent is then positioned inside the vessel to ensure that it maintains the enlarged diameter once the expanding balloon is removed.

On the other hand it is known to use miniaturized devices for performing diagnostic or research measurement inside the body of a human or an animal. Such devices are in general inserted inside a blood vessel or another body lumen by a suitable catheter. This procedure, even if it is only moderately invasive, must be performed in a medical establishment and does not allow prosecuting the measurement for an extended period of time or during patient's normal activities.

Moreover the known stenting devices are in general suitable for definitive implantation only. While safe and reliable procedures to position a stent into a body lumen are well established, this is not generally true for recovering or repositioning an already implanted device. Once a stent is deployed its emplacement is considered definitive and recovering or replacing it would often require invasive surgery.

BRIEF SUMMARY OF THE INVENTION

An aim of the present invention is to provide a practical and safe device for performing accurate inner measurements for diagnostic, research or therapy, without interfering with patient's normal activities and in a minimally invasive way.

Another object of the present invention is to provide a replaceable intraluminal or intravascular device, which can safely and easily be recovered from its position inside the body, or moved to a different position, without the necessity of invasive techniques.

These objects are attained by the devices and method of the independent claims in the corresponding categories, while the remaining claims deal with preferred and alternatives embodiment and examples. In particular, said objects are attained by an implantable intraluminal or intravascular device, i.e. for placement in a body lumen, preferably in a blood vessel, comprising:
  an expandable section having a variable dimension, said variable dimension allowing a compressed value $D_c$ for delivery to said body lumen and an expanded value $D_e$, larger than said compressed value $D_c$, for implantation in said body lumen;
  a link section at one end of said device, comprising a grip, for joining said device to a catheter, and for applying an axial force on said device;
  at least one sensor permanently joined to said device;
  wherein said device is arranged for reacting to an axial pulling force to said grip, by assuming said compressed value of said variable dimension, for retrieval or repositioning of said implantable device;

and by an apparatus for positioning an implantable device according to claim 1, comprising:
  a flexible catheter, inserted into a flexible sleeve;
  a grasp section, fixed to the tip of said catheter, for cooperating with said link section of said implantable device, said clasp section comprising at least two opposed flexible fingers;
  said flexible sleeve interacting with said flexible fingers for opening and closing them on said link section, and interacting with said expandable section for reducing said variable dimension of said implantable device.

BRIEF DESCRIPTION OF THE DRAWINGS

The invention will be better comprised from the study of the following description and claims and with reference to the appended figures wherein:

FIG. 1 shows an implantable device according to the invention, connected to a delivery/recovery apparatus according to the invention;

FIG. 3 represent an alternative embodiment of the implantable device according to the invention, comprising a flexible tether.

FIGS. 4a and 4b show another embodiment of the invention wherein the implantable device comprises a tubular mesh;

DETAILED DESCRIPTION OF THE INVENTION

Figure 2A:
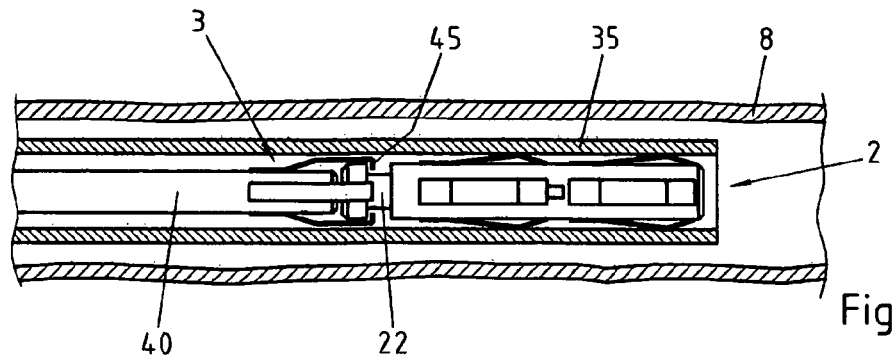
FIGS. 2a to 2d represent a sequence of actions describing the use of the device and the apparatus of FIG. 1.

According to a first embodiment of the present invention, the implantable device 2 comprises a core 10, of elongated shape, on which are disposed at least a plurality of elastic struts 6 which can assume all the positions between the fully released configuration visible in FIG. 1, in which the struts 6 extend radially from the body 10, and a compressed configuration, in which the struts are almost in full contact with the core 10.

The transversal diameter of the device 2 is therefore variable according to the configuration of the flexible struts 6. In their fully released position the struts 6 define the maximum expanded diameter $D_e$ of the device, while the compressed diameter $D_c$ is obtained when the struts 6 are in full contact with the core 10.

In this particular example of the invention the struts 6 are in number of 8, and disposed, as shown on FIG. 1, in two levels, each comprising four radial struts. The skilled person will understand however that the number of struts and their disposition could easily be modified, according to the circumstances and the destination of the implantable device 2.

The link section 20 is located at one extremity of the core 10, and its function is to allow repeatable engagement and connection with the grasp section placed on the delivery/recovery apparatus 3, also visible on FIG. 1. The link section comprises, in this embodiment of the invention, a round/cylindrical head 21, joined to the core by a relatively narrow neck 22.

The delivery/recovery apparatus 3 comprises a flexible catheter 40, enclosed in a flexible sleeve 35. On the tip of the catheter 40 is fixed a grasping device composed by the four flexible fingers 45. According to the relative position of the catheter 40 in the sleeve 45 the fingers can be retracted inside the sleeve 45, in which case they assume the closed configuration represented in FIG. 1, or they can extend forward from the sleeve 45, in which case their elasticity forces them in the open configuration shown on FIG. 2c.

The functioning of the implantable device 2 and of the apparatus 3 will now be explained in relation with FIGS. 2a-2d, showing a typical implantation sequence.

In FIG. 2a is visible the implantable device 2, connected to the catheter 40 by the fingers 45 closed on the neck 22 of the link section. The device 2 is fully retracted inside the sleeve 35.

In this configuration the sleeve 35 is inserted into the human or animal body, and guided until the tip of the apparatus 3, now containing the device 2, is at the place chosen for the implantation. The progress of the device into the body can for example be monitored and followed using conventional X-ray techniques. To this effect the device 2 and the delivery/recovery apparatus 3 may be equipped with radio-opaque marks.

Figure 2B:
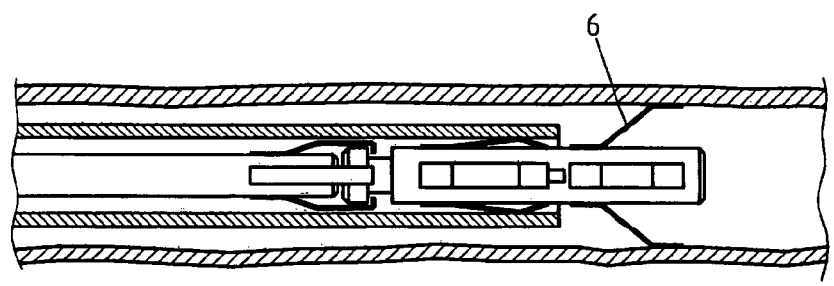

Once the position of the device 2 is satisfactory, the operator retracts the sleeve 35 (FIG. 2b). The device 2 is still connected and axially maintained by the catheter 40. In this way the struts 6, now free from the sleeve 35, open themselves and anchor the device 2 inside the blood vessel 3.

Figure 2C:
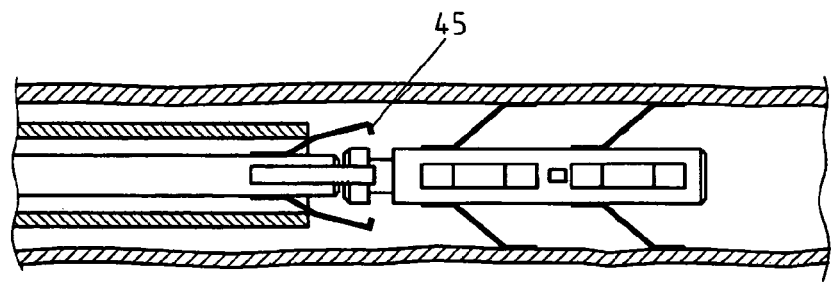

By continuing the retraction of the sleeve 35 the fingers 45 finally get free, and open themselves (FIG. 2c). The device 2 is now detached from the catheter 40.

Finally the catheter 35 is pulled back, and the fingers 45 retracted inside the sleeve 35. In this configuration the apparatus 3 can be extracted from the body, leaving the implantable device 2 in place in the body lumen 8. Accordingly, the implantable device is in a position in which the elongated body is essentially aligned with an axis of the body lumen.

Figure 2D:
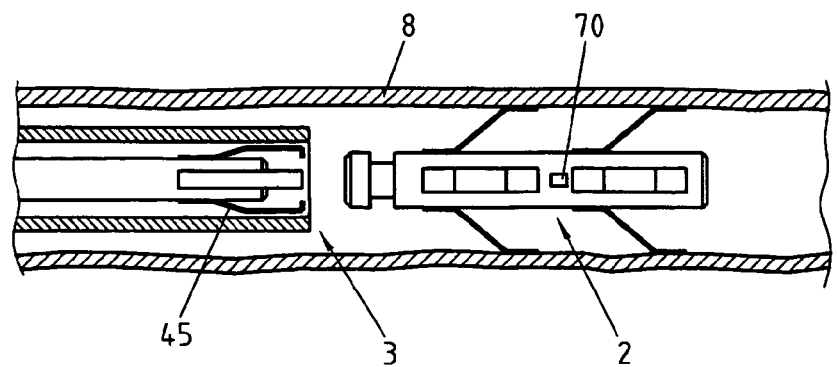

A recovery sequence involves all the above steps in reverse order. Initially the delivery/recovery apparatus 3 is inserted in the body lumen 8, with the grasp section fully retracted inside the sleeve 35 (FIG. 2d). The catheter 45 is then pushed out of the sleeve 35 in order to expose and open the fingers 45 (FIG. 2c). During this phase the fingers 45 touch the walls of the body lumen 8, and align the tip the catheter 35 with the axis of the body lumen, simplifying the connection between delivery/recovery apparatus 3 and the implantable device 2. Once the tip of the catheter 35 is in contact with the link section of the implantable device, the sleeve 35 is advanced (FIG. 2b), in order to close the fingers 45 on the neck 22, thereby locking and aligning the catheter 35 and the implantable device 2. Finally the edge of the sleeve 35 enters in contact with the struts 6 and forces them in the compressed configuration. The device 2 is now released from the lumen 8 and can be recovered inside the sleeve 35.

Figure 5:
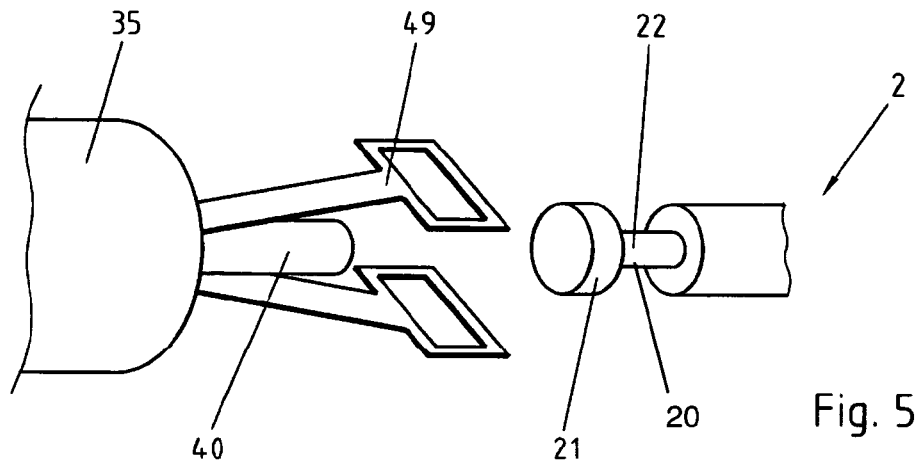
FIGS. 5 and 6 illustrate two different fashions of realizing the connexion between the implantable device and the positioning apparatus of the invention.

The grasp section of the delivery/recovery apparatus 3 can of course take also other forms, different from the hook-shaped fingers of FIG. 1. In a variant of the present embodiment represented on FIG. 5, the grasp section comprises two rectangular or oval loops 49.

Figure 6:
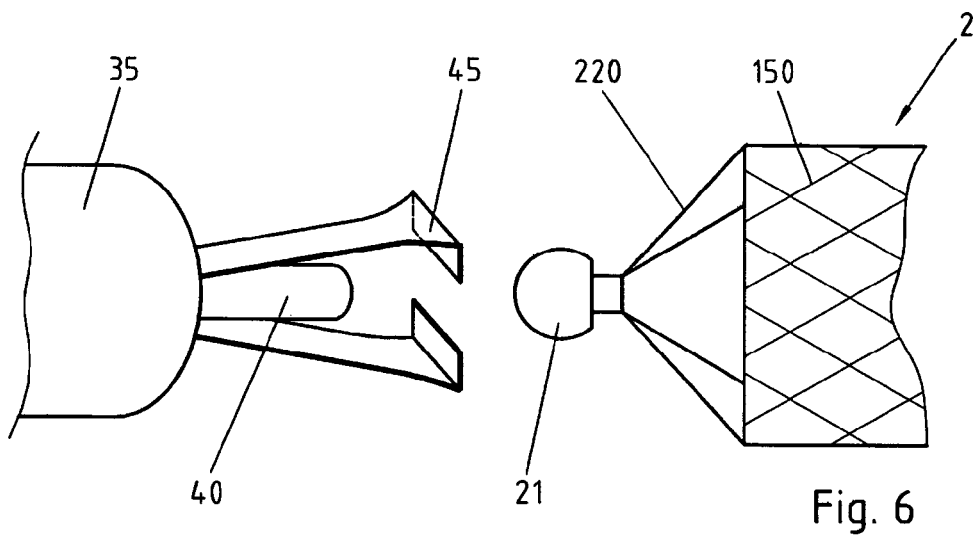
Figure 8:
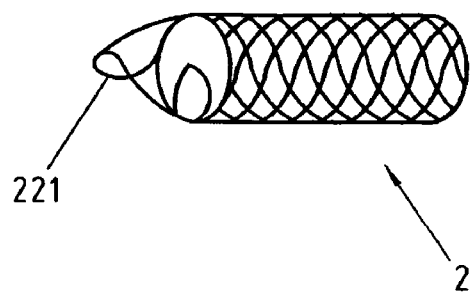

The link section 20 of the device 2 can also take other forms than the round head if FIG. 1. For example, in the variant of FIG. 6, which will be explained in more detail later, the head 21 has the shape of a ball. In the example visible on FIG. 8 the link section comprises a wire loop 221.

The present invention is however not limited to the shapes described here by way of example for the join section of the device 2 and the grasp section of the delivery/recovery apparatus 3, but comprises as well all the many different shapes adapted to interoperate together for the realization of the invention.

The device 2 further comprises at least a permanently attached sensor 70. For example the sensor 70 may measure a physical property, like blood pressure sensor, fluid flow, temperature or electric heart or muscle activity. The sensor 70 may also record a chemical blood parameter, like pH, glycaemia, electrolytes or gas concentration.

Preferably the sensor 70 communicates with an external readout unit (not shown) via a wireless connection. In this way the parameters acquired by the sensor 70 can be accessed whenever necessary, or automatically logged on a periodical basis in the readout unit for later analysis.

If requested, the readout unit may be arranged to trigger an alarm signal in case an abnormal situation, calling for urgent medical care is detected.

Advantageously the wireless link between the external readout unit and the sensor 70 could also provide the necessary energy source for the sensor operation. The link could for example comprise a backscattering passive transponder.

In this variant of the invention, the sensor 70 is only active when the readout unit sends an electromagnetic flux toward the implanted device 2. In this case the electrical signal picked up by the transponder antenna serves, after rectification and conversion, to supply the sensor 70. The requested measurement is then sent back to the readout unit by backscattering modulation or other transmission techniques.

Other wireless communication techniques, like for example HF, acousto-magnetic, electromagnetic, swept-RF or Macro-wave or others are also possible and comprised in the present invention.

By using a passive transponder, the need of an energy source in the implantable device is avoided, thus reducing the size of the device 2 and the hazard connected with electrochemical batteries. Autonomous energy sources may however also be employed, according to the circumstances.

In an alternative, not represented, variant of the present invention, the data recorded by the sensor 70 are logged in a permanent memory included in the implantable device 2. In this case no real-time telemetry link is required. Instead the data are analyzed in a second moment, when the implantable device 2 is removed from the patient's body.

According to this variant embodiment of the invention, the implantable device 2 may comprise an autonomous source of electrical energy, for example an electrochemical battery. Alternately, the implantable device 2 may be alimented by an external source, via a magnetic link or another wireless energy transmission technique.

Advantageously, the sensor 70 may communicate with another implanted device present in the patient's body, via a wireless connection. Thanks to this communication, an implantable device may adapt its operating parameters depending on data received from the sensor 70. Such implantable device may include for example a cardiac stimulator, a drug delivery device, or any other device. The data transmitted via the wireless link by the sensor 70 to the implantable device may be representative of any significant body parameter like for example blood or fluid pressure, sugar concentration, or any other significant clinical parameter.

Advantageously the device of the invention comprises also a radiofrequency antenna for the wireless connection. According to circumstances the antenna may be incorporated in the device body or comprise for example a flexible wire protruding from the device body, a mesh antenna, a linear antenna or others.

According to another embodiment of the present invention, represented on FIG. 3, the sensor 70 is not rigidly joined to the device 2, but rather connected to it by a flexible tether 50.

This embodiment of the invention allows monitoring of body parameters in places that, due to their conformation or for other reason, would not be suitable for directly placing a device. An example of application for this embodiment of the present invention would be the monitoring of blood pressure in an aneurism According to another embodiment of the present invention not represented in the figures, the device 2 includes a reservoir of a biologically active substance, which can be selectively put in fluid contact with the body lumen 8 by an appropriate command from an external unit in wireless communication with the implantable device 2. This embodiment of the invention comprises a hollow reservoir and an electrically actionable valve realized with known micro-fluidic and MEMS (microelectromechanical systems) techniques, for example by 2D or 3D photolithography, or by a LIGA process.

In another variant embodiment the device may contain elements loaded with a biologically active substance, which is passively released in the body, until the device is extracted, or the supply is used up.

According to the embodiment of the invention represented on FIGS. 4a and 4b, the body of the implantable device 2 comprises a tubular elastic mesh 150 of biocompatible wire. The tubular mesh 150 has an expanded configuration, allowing it to adhere closely to the inner walls of the blood vessel 8, yet is sufficiently elastic to be compressed inside the sleeve 35 of the delivery/recovery apparatus 3. The link section consists, in this embodiment of the present invention, of a ball 21, connected to the mesh 150 by at least one wire 220, as it is visible on FIG. 6.

Figure 7:
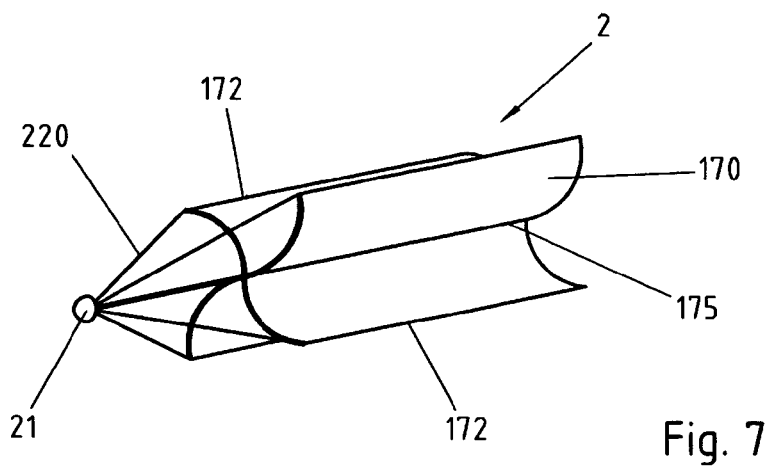
FIGS. 7, 8, 9, 10 and 11 shows other embodiments of the implantable device according to the invention.

According to another embodiment of the present invention represented on FIG. 7, the device 2 comprises a plurality of curved smooth membranes 170 joined together by a common central edge 175. The outer edges 172 of the membranes 170 lie, in the deployed extended configuration, on the inner walls of the blood vessel 8, thereby securing the device 2 in place. To recover the device 2 the membranes 170 are bent elastically and/or rolled one on each other, by the combined action of the catheter 35 pulling on the ball 21 and of the edge of the sleeve 35 pushing on the wires 220, until the device 2 is fully retracted inside the sleeve 35. In this particular embodiment, the exposed surfaces are smooth and parallel to the fluid current, thereby opposing a low flow resistance, without disturbing laminar flow.

Figure 9:
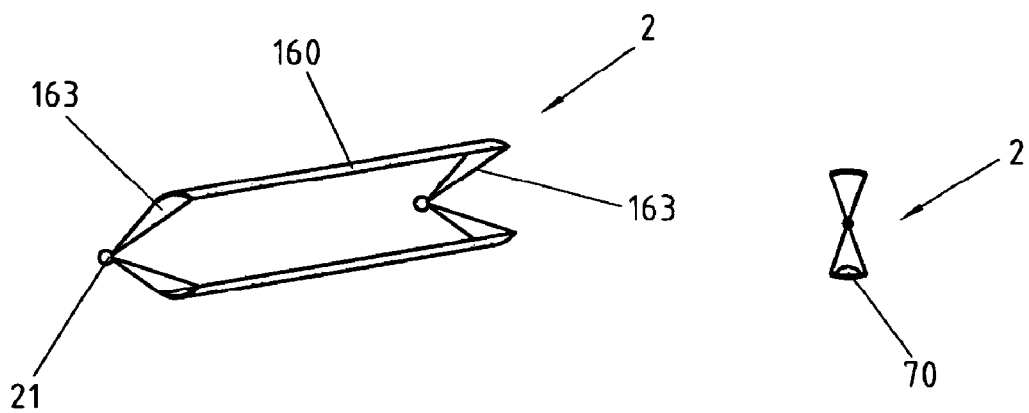

According to another embodiment of the present invention represented on FIG. 9, the device 2 comprises two flexible lateral plates 160, having a cylindrical surface, joined by the triangular or conical flexible surfaces 163. In the expanded state the lateral surfaces 160 contact the inner wall of the body lumen 8 and maintain the device in the desired position. The creases between lateral plates 160 and the connecting surfaces 163 can bend, compressing the device 2 inside the sleeve 35, as in the other embodiments.

Figure 10:
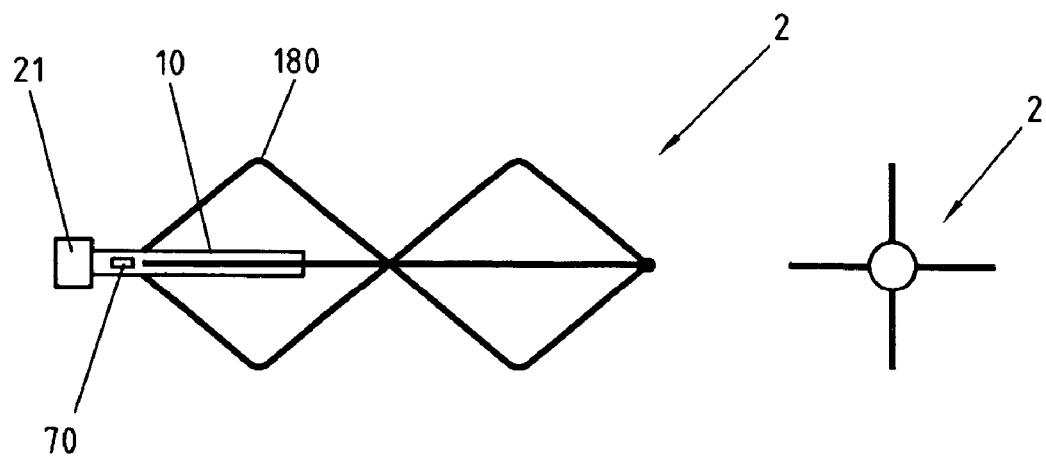

According to another embodiment of the present invention represented on FIG. 10, the device 2 comprises an elongated core 10 and at least one flexible wire 180 comprising straight and bent sections, whose flexibility allows a compressed configuration for fitting inside the sleeve 35 and an expanded configuration for anchoring inside the body lumen 3 having a lateral dimension larger than the lateral dimension of said compressed configuration.

Figure 11:
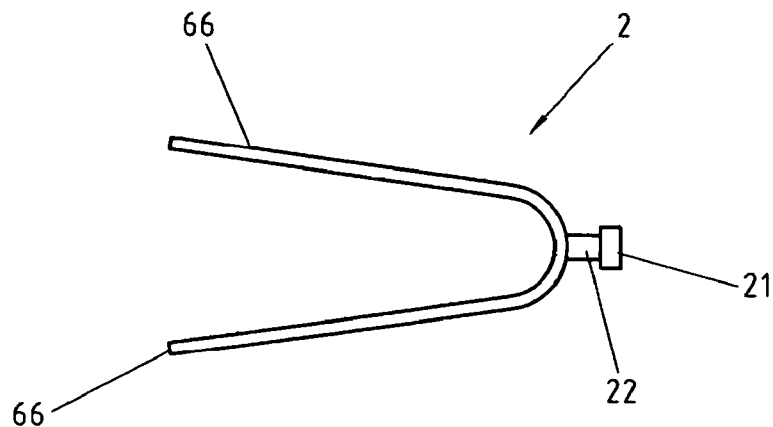

FIG. 11 represents a further embodiment of the present invention, in which the implantable device comprises two flexible arms 66, joined as to form a flexible "U", and the join section fixed on the curved section of the "U"

Figure 12:
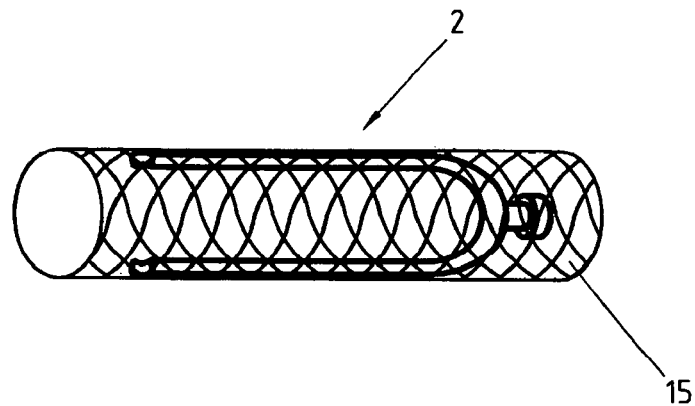
FIG. 12 shows an application of the device of the invention in conjunction with a vascular stent.

FIG. 12 shows an application of the present invention in which the implantable device 2 is inserted in a permanent or semipermanent angioplasty stent 15. In this case the particular embodiment of FIG. 11 is shown, inside a tubular stent 15. The skilled person will understand, however, that all presented embodiment of the invention may be adapted for use in this manner. In this particular application, the device of the invention can for example be placed for a limited time, after an angioplasty operation, in the expanded body vessel. Thanks to this aspect of the invention it is possible to monitor or log blood pressure, flow constriction, or other clinical parameters, or deliver drugs in situ.

Independently from the expansive action of the stent 15, it may be desirable in certain cases to provide for an interface element 15 between the implantable device 2 and the walls of the body lumen into which the device 2 is placed. The interface element 15 may include for example a cylindrical sleeve as represented on FIG. 12, optionally treated with appropriate substances for preventing or limiting a tissue growth at the implant site, thereby reducing the risk of embolism during the recovery of the device 2.

The interface element 15 may be recovered with the device 2, or may be left in situ permanently or until a later moment. Other forms of interface elements are however possible and readily devisable by the skilled in the art.

Figure 13:
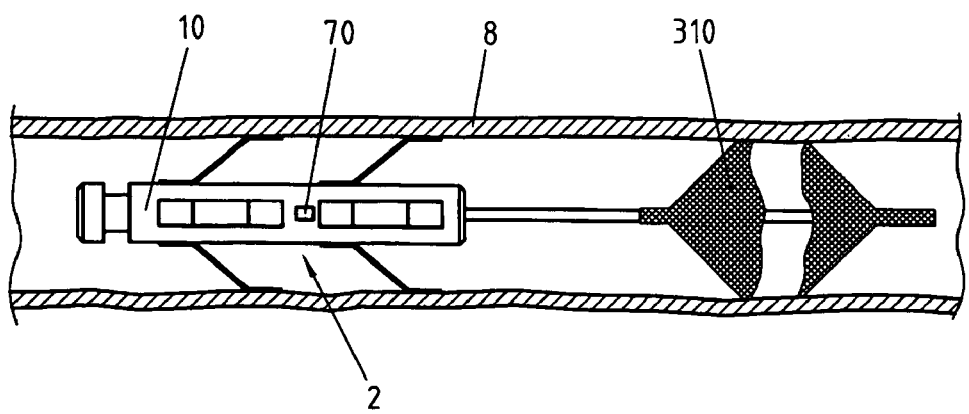
FIG. 13 shows an implantable device according to the invention and comprising a vascular filter.

A further embodiment of the present invention is now described with reference to FIG. 13. According to this embodiment the implantable device 2 comprises an embolism protection device 310.

During the positioning or recovery of the device of the invention, there is a risk that emboli dislodged by the procedure will migrate through the circulatory system and cause infarction, strokes or other medical conditions. Similarly dangerous conditions may arise while the device is implanted in the foreseen location, according to the circumstances.

The protection device 310 prevents emboli from migrating through the circulatory system and may consist in a filtering device, capable of capturing eventual embolic particles, while allowing essentially unimpeded blood flow. An example of such vascular filters is described, among others, in International Patent Application WO03/011185, which is hereby incorporated by reference. Many other filters means are however possible and comprised in the scope of the present invention. Other devices, like for example balloons or other occlusion means are also enclosed in the scope of the present invention. According to the necessity, the protection device can be positioned distally or proximally with reference to the device body 10.

One advantage of the present invention is that the implantable intraluminal or intravascular device 2 is releasably connected to a positioning apparatus for permanent or semipermanent delivery within a body lumen. It is however to be understood that the implantable device of the invention can as well be employed, if required or convenient, while still connected to the positioning apparatus 3. For example during the positioning or retrieval phases, or when a temporary diagnostic or therapeutic action is required.

The implantable device 2 of the invention may further provide an attachment site for connecting a removable part thereto. The removable part may include for example a drug-release element, which need to be renewed after a certain time, or comprise the sensor 70, or also comprise additional sensors or other diagnostic or clinical devices which can be connected to the implantable device 4 and removed at will by appropriate endoscopic or surgical techniques.

The attachment site may comprise any suitable attachment means, for connecting the removable part and the sensor. For example said attachment means may comprise a threaded connection or a clip connection, or others.

The present invention has been described by means of specific examples and embodiments. It will be understood however, by the skilled of the art, that various alternatives may be used and equivalents may be substituted for elements described herein, without deviating from the scope of the invention. Modifications may be necessary to adapt the invention to a particular situation or to particular materials or sensors without departing from the scope of the invention. It is intended that the invention not be limited to the embodiment presented herein by way of the example, but that the claims be given their broadest interpretation to cover all the embodiments, literal or equivalent, discussed herein.

The invention claimed is:

1. A combination of: an implantable intraluminal or intravascular device for use in a body lumen having walls, and an apparatus for positioning said implantable device in the body lumen, the combination comprising:
    said implantable device comprising:
        an elongated body;
        an expandable section having elongated straight struts with a proximal section connected to said elongated body and extending at an angle to said elongated body, and a distal section extending parallel to said elongated body, said expandable section having a variable dimension allowing a compressed value for delivery to said body lumen and an expanded value, larger than said compressed value, for implantation in said body lumen so that the proximal sections press the distal sections outwardly against said body lumen walls to removably engage the device with said body lumen;
        a link section, at one end of said device comprising a grip, for detachably joining said device to a catheter, and for applying an axial force on said device, wherein said grip comprises a head having a transversal dimension, and a neck connecting said head to said device, having a dimension smaller than said transversal dimension of said head;
        at least one sensor joined to said device;
        wherein said device is arranged for reacting to an axial pulling force to said grip, by assuming said compressed value of said variable dimension, for retrieval or repositioning of at least part of said implantable device; and
    said apparatus comprising:
        a flexible catheter, inserted into a flexible sleeve;
        a grasp section, fixed to the tip of said catheter, for cooperating with the link section of said implantable device, said grasp section comprising at least two opposed flexible fingers;
        said flexible sleeve interacting with said flexible fingers for opening and closing said flexible fingers on said link section of said implantable device, and interacting with an expandable section of said implantable device for reducing the variable dimension of said implantable device.

2. The implantable intraluminal or intravascular device of claim 1, comprising a plurality of elastic struts having a released configuration, in which said elastic struts radially protrude from said elongated body, and a compressed position, in which said elastic struts are closer to said elongated body.

3. The implantable intraluminal or intravascular device of claim 2, wherein the distal sections are unattached to protrude out from said elongated body in the released configuration.

4. The implantable intraluminal or intravascular device of claim 1, comprising a tubular mesh of elastic wire, whose diameter allows a compressed value and an expanded value, larger than said compressed value.

5. The implantable intraluminal or intravascular device of claim 1, comprising a plurality of curved smooth membranes, parallel to the main axis of said device, allowing essentially unobstructed fluid flow through said body lumen.

6. The implantable intraluminal or intravascular device of claim 1, comprising a plurality of flexible lateral surfaces, for anchoring said device within said body lumen, bendably joined by a plurality of radial connection elements allowing a compressed configuration having a lateral dimension and an expanded configuration having a lateral dimension, larger than said lateral dimension of said compressed configuration.

7. The implantable intraluminal or intravascular device of claim 1, comprising and at least one flexible wire comprising straight and bent sections, whose flexibility allows a compressed configuration having a lateral dimension and an expanded configuration having a lateral dimension, larger than said lateral dimension of said compressed configuration.

8. The implantable intraluminal or intravascular device of claim 1, wherein said sensor includes a communication device to communicate with an external readout unit and/or to communicate with another implanted device by a wireless link.

9. The implantable intraluminal or intravascular device of claim 8, wherein said wireless link also provides energy supply for said sensor.

10. The implantable intraluminal or intravascular device of claim 8, further comprising a reservoir, which can selectively be put in fluid communication with said body lumen upon a command received on said wireless link.

11. The implantable intraluminal or intravascular device of claim 1, further comprising at least one release means, for releasing at least one substance comprised in said release means.

12. The apparatus of claim 1, wherein the expanded value of the expandable section is greater than an outer diameter of the apparatus for positioning.

13. A combination of: an implantable intraluminal or intravascular device and an apparatus for positioning said implantable device in a body lumen having walls,
    said implantable device comprising:
        an elongated body;
        an expandable section having elongated straight struts with a proximal section connected to said elongated body and extending at an angle to said elongated body, and a distal section extending parallel to said elongated body, said expandable section having a variable dimension allowing a compressed value for delivery to said body lumen and an expanded value, larger than said compressed value, for implantation in said body lumen so that the proximal sections press the distal sections outwardly against the body lumen walls to removably engage the device with said body lumen;
        a link section, at one end of said device comprising a grip, for joining said device to a catheter, and for applying an axial force on said device;

at least a sensor joined to said device;
said apparatus comprising:
- a flexible catheter, inserted into a flexible sleeve;
- a grasp section, fixed to the tip of said catheter, for cooperating with said link section of said implantable device, said grasp section comprising at least two opposed flexible fingers;
- said flexible sleeve interacting with said flexible fingers for opening and closing said flexible fingers on said link section;

wherein said flexible sleeve interacts with said implantable device by forcing the expandable section to assume said compressed value of said variable dimension, when said device is pulled by said flexible catheter into said flexible sleeve.

14. The implantable intraluminal or intravascular device of claim 13, wherein said sensor is permanently joined to said device.

15. The implantable intraluminal or intravascular device of claim 13, comprising an attachment site, for connecting a removable part thereto.

16. The implantable intraluminal or intravascular device of claim 13, wherein at least a part of said sensor is flexibly connected to said device, by a flexible tether.

17. The implantable intraluminal or intravascular device of claim 13, wherein said grip is connected to said device by at least one wire.

18. The implantable intraluminal or intravascular device of claim 13, wherein said grip comprises a loop of wire.

19. The implantable intraluminal or intravascular device of claim 13, further comprising an embolic protection device.

20. The implantable device of claim 19, wherein said embolic protection device comprises filter means for retaining embolic particles.

21. The implantable intraluminal or intravascular device of claim 13, wherein said sensor comprises at least one of: a temperature sensor; a pressure sensor; a chemical sensor, a fluid flow sensor, an ECG sensor, a pH sensor, an electrolyte sensor, a wireless communication device.

22. The combination of claim 13, wherein the expanded value of the expandable section is greater than an outer diameter of the apparatus for positioning.

23. A method for sensing a parameter within a body lumen comprising the steps of:
providing an implantable intraluminal or intravascular device with an elongated body including:
- an expandable section having elongated straight struts with a proximal section connected to the elongated body and extending at an angle to said elongated body, and a distal section extending parallel to the elongated body, the expandable section having a variable dimension, said variable dimension allowing a compressed value for delivery to said body lumen and an expanded value, larger than said compressed value, for implantation in said body lumen;
- a link section, at one end of said device comprising a grip, for detachably joining said device to a catheter, and for applying an axial force on said device, wherein said grip comprises a head having a transversal dimension, and a neck connecting said head to said device, having a dimension smaller than said transversal dimension of said head;
- at least one sensor joined to said device;

wherein said device is arranged for reacting to an axial pulling force to said grip, by assuming said compressed value of said variable dimension, for retrieval or repositioning of at least part of said implantable device, providing an apparatus for positioning said implantable device in the body lumen, including:
- a flexible catheter, inserted into a flexible sleeve;
- a grasp section, fixed to the tip of said catheter, for cooperating with said link section of said implantable device, said grasp section comprising at least two opposed flexible fingers;
- said flexible sleeve interacting with said flexible fingers for opening and closing said flexible fingers on said link section;

wherein said flexible sleeve interacts with said implantable device by forcing the expandable section to assume said compressed value of said variable dimension, when said device is pulled by said flexible catheter into said flexible sleeve.

* * * * *